Figure 1:
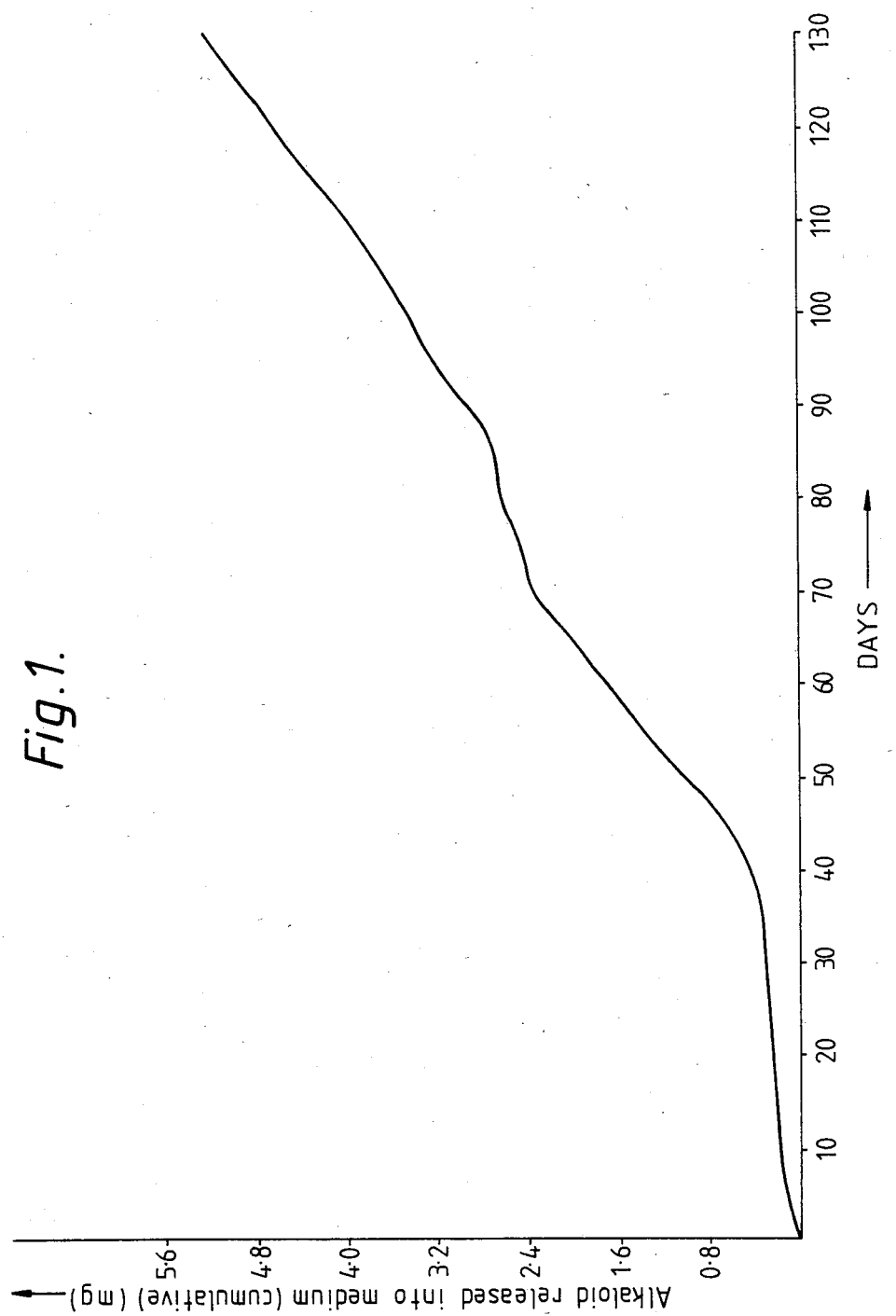

United States Patent [19]

Rosevear et al.

[11] Patent Number: 4,578,351

[45] Date of Patent: * Mar. 25, 1986

[54] PRODUCTION OF CHEMICAL COMPOUNDS WITH IMMOBLIZED PLANT CELLS

[75] Inventors: Alan Rosevear; Christopher A. Lambe, both of Wantage, England

[73] Assignee: United Kingdom Atomic Energy Authority, England

[*] Notice: The portion of the term of this patent subsequent to Jun. 5, 2001 has been disclaimed.

[21] Appl. No.: 622,761

[22] Filed: Jun. 20, 1984

Related U.S. Application Data

[63] Continuation of Ser. No. 361,107, Mar. 23, 1982, abandoned.

[30] Foreign Application Priority Data

Apr. 21, 1981 [GB] United Kingdom ................ 8110421

[51] Int. Cl.⁴ .................... C12P 1/00; C12P 33/00; C12P 21/00; C12N 11/04
[52] U.S. Cl. ........................................ 435/41; 435/52; 435/68; 435/178; 435/180; 435/182; 435/240
[58] Field of Search ................ 435/41, 174, 177, 178, 435/180, 182, 52, 68, 240

[56] References Cited

U.S. PATENT DOCUMENTS

| | | | |
|---|---|---|---|
| 3,849,253 | 11/1974 | Harvey et al. | 435/182 |
| 3,859,169 | 1/1975 | O'Driscoll et al. | 435/182 |
| 3,962,038 | 6/1976 | Kamashima et al. | 435/182 X |
| 4,452,892 | 6/1984 | Rosevear | 435/178 X |

FOREIGN PATENT DOCUMENTS 22434 1/1981 European Pat. Off. .

OTHER PUBLICATIONS

Kierstan et al., Biotechnology and Bioengineering, vol. XIX, 1977, pp. 387–397.
Brodelius et al., FEBS Letters, vol. 122, No. 2, 1980, pp. 312–316.
Brodelius et al., FEBS Letters, vol. 103, No. 1, 1979, pp. 93–97.
Morikama et al., Biotechnology and Bioengineering, vol. XXI, 1979, pp. 261–270.
Karube et al., Biotechnology and Bioengineering, vol. XXI, 1979, pp. 253–260.

*Primary Examiner*—David M. Naff
*Attorney, Agent, or Firm*—Larson and Taylor

[57] ABSTRACT

Plant cells containing intra-cellular chemical compounds are induced to excrete the compounds by maintaining the cells in a sufficiently high cell density. A sufficiently high cell density is preferably maintained by immobilizing the cells in a modified polyacrylamide gel containing polyacrylamide and a minor amount of xanthan gum or sodium alginate. Vinca plant cells can be immobilized to produce the chemical compounds, ajmalicine and serpentine. Alternative to immobilizing the cells, a sufficiently high cell density can be provided by maintaining the cells in a permeable enclosure such as a woven nylon bag.

9 Claims, 1 Drawing Figure

PRODUCTION OF CHEMICAL COMPOUNDS WITH IMMOBLIZED PLANT CELLS

This is a continuation of application Ser. No. 361,107 filed Mar. 23, 1982, now abandoned.

The present invention relates to the production of chemical compounds and particularly to the biological production of chemical compounds.

According to one aspect of the present invention there is provided a process for the production of a chemicalcompound by use of cells comprising maintaining viable cells, containing a chemical compound, in sufficiently close proximity to cause the cells to excrete the chemical compound and recovering the chemical compound substantially without damage to the cells.

Chemical compounds produced in cells (e.g. eukaryotic cells such as plant and animal cells) can be of considerable medical and industrial value. In known methods, cells have been grown, harvested and extracted to remove intra-cellular chemical compounds and give a soluble fraction from which chemical compounds can be recovered.

Also in known methods of recovering chemical compounds from cells a membrane modifying agent (e.g. chloroform) is used to promote extraction of the chemical compounds.

The use of such agents gives rise to substantial cell damage and in many circumstances the destruction of the cells. For example, the use of chloroform can be shown to cause massive lysis of the cells.

In accordance with the present invention it has been found that, surprisingly, cells can be induced to excrete intra-cellularly produced chemical compounds if they are brought together and maintained in close proximity to a sufficient extent (i.e. if they are maintained in a sufficiently high cell density).

The mechanism by which the cells are induced to excrete chemical compounds is not fully understood. However, it is evident that the behaviour of the cells is modified by maintaining them sufficiently close together (i.e. in a sufficiently high cell density) with the result that chemical compounds normally retained within the cells are excreted therefrom. The degree of close proximity required to achieve excretion of the chemical compound can be determined experimentally for given cells and conditions.

In this specification "maintained in close proximity" means "maintained in sufficiently close proximity to cause the cells to excrete the chemical compound". It is to be understood that "close proximity" in accordance with the present invention means artifically induced close proximity and does not embrace any close proximity when occurring in nature in a whole plant or animal body. It is to be understood that artifically induced close proximity does not exclude cell growth (i.e. cell division and/or increase in cell size). Thus, for example, in accordance with the present invention cell growth may take place after immobilisation of cells as disclosed hereinafter.

By way of example, cells may be grown by suspension or tissue culture to be single cells or small cell clumps of undifferentiated tissue before being maintained in close proximity in accordance with the present invention.

Preferably the cells are grown (e.g. by tissue culture) to the point in their growth cycle where secondary metabolism is established such that the chemical compound is being produced in the cells before they are maintained in close proximity.

It has been found, in accordance with the present invention, that cells maintained in close proximity before this point tend to produce less chemical compound than cells which are maintained in close proximity only after secondary metabolism has been established.

Also it is preferred that the cells are maintained in close proximity before the point in the growth cycle where any substantial senescence occurs.

It has been found, in accordance with the invention, that cells maintained in close proximity before the onset of senescence tend to have a longer useful life-time (i.e. remain viable and chemical compound producing for a longer period) than those that are not maintained in close proximity until later in the growth cycle.

It is preferred that cells to be taken and maintained in close proximity are cells which have reached a point in their growth cycle corresponding to the logarithmic to mid-logarithmic phase.

Subsequently to being maintained in close proximity cells may be maintained in near-zero growth conditions (e.g. by use of an environment lacking growth hormones) and used to produce chemical compounds over long periods (e.g. 50 to 100 days).

In accordance with one embodiment of the present invention there is provided a process for the production of a chemical compound by use of cells comprising contacting a feed solution with viable cells under conditions such that the chemcial compound is produced in the cells, maintaining the cells in sufficiently close proximity to cause the cells to excrete the chemical compound and recovering the chemical compound substantially without damage to the cells.

The term "viable" as used herein in relation to cells embraces the condition wherein the cells are alive and capable of producing metabolites. The term does not necessarily imply that the cells have to be capable of reproduction.

The cells may be maintained in sufficiently close proximity by any suitable means.

For example, in accordance with one embodiment of the present invention, the cells are maintained in close proximity by immobilising them.

Preferably the cells are grown until secondary metabolism is established such that the chemical compound is being produced in the cells before they are immobilised.

It has been found, in accordance with the present invention, that cells immobilised before this point tend to produce less chemical compound then cells which are imobilised only after secondary metabolism has been established.

Also it is preferred that the cells are immobilised before the point in the growth cycle where any substantial senescene occurs.

It has been found, in accordance with the invention, that cells immobilised before the onset of senescence tend to have a longer useful life-time (i.e. remain viable and chemical compound producing for a longer period) than those that are immobilised later in the growth cycle.

It is preferred that cells are immobilised in the logarithmic to mid-logarithmic phase of their growth cycle.

Subsequently to being immobilised cells may be maintained in near-zero growth conditions (e.g. by use of an environment lacking growth hormones) and used to produce chemical compounds over long periods (e.g. 50 to 100 days).

It is preferred that the cells are immobilised by a method disclosed in co-pending British Patent Application No. 8126579 (UKAEA) which claims priority from British Patent Application No. 8029343 (UKAEA) or by a method disclosed in co-pending British Application No. 8126580 (UKAEA) which claims priority from British Patent Application No. 8029344 (UKAEA).

A detailed discussion of immobilisation can be found in British Patent Application Nos. 8126579 and 8126580 hereinbefore mentioned, the disclosures of which are hereby incorporated by reference into this Specification.

In British Patent Application No. 8126579 there is disclosed, inter alia, the following:

"A method for the preparation of a composite material containing an immobilised biologically active species which comprises applying a gel precursor to a support material, the said gel precursor containing a biologically active species or precursor therefor, and gelling the gel precursor to form a composite material comprising the support material, a gel retained on the support material and, immobilised in the gel, the biologically active species, the rheological properties of the gel precursor being selected (i) to facilitate application of the gel precursor to the support material and (ii) to facilitate retention of the gel precursor on the support material prior to and during the gelling and/or to inhibit the sedimentation of biologically active species prior to, and during gelling."

In accordance with British Patent Application No. 8126580 there is disclosed, inter alia, the following:

"A method for the preparation of a composite containing an active material which comprises applying an active material composition having selected rheological properties to a support material and providing a cover for the active material composition on the support material, the cover being in the form of a permeable membrane."

It will be appreciated that in Application Nos. 8126579 and 8126580 hereinbefore mentioned the terms "biologically active species" and "active material" respectively embrace cells.

Thus, for example, cells may be immobilised by a method which comprises applying a gel precursor to a support material, the said gel precursor containing cells, and gelling the gel precursor to form a composite material comprising the support material, a gel retained on the support material and cells immobilised in the gel, the rheological properties of the gel precursor being selected (i) to facilitate application of the gel precursor to the support material and (ii) to facilitate retention of the gel precursor on the support material prior to and during the gelling and/or to inhibit the sedimentation of cells prior to, and during gelling.

By way of further example cells may be immobilised by a method which comprises applying an active material composition having selected rheological properties to a support material and providing a cover for the active material composition on the support material, the cover being in the form of a permeable membrane and the active material composition containing cells.

Cells may be immobilised in sufficiently high cell density (i.e. concentration) to achieve the sufficiently close proximity to cause the cells to excrete the chemical compound.

Alternatively, an innoculum of cells (e.g. suspension cultured cells) containing a very low cell density may be immobilised and then allowed to grow (i.e. divide and/or increase in size) to a sufficiently high concentration to achieve the sufficiently close proximity to cause the cells to excrete the chemical compound.

Immobilisation makes it possible to maintain viable cells (e.g. produced by suspension culture) in close proximity without limiting nutrient supplies as might occur if cells were merely allowed to settle or grow as large calluses.

Other means may be utilised to maintain the cells in close proximity. Thus, the cells may be maintained in close proximity by means of enclosure in a permeable enclosure (e.g. a woven nylon bag).

By way of further example cells can be induced to excrete intra-cellularly produced chemical compounds by arranging for a sufficiently high cell population to be present in a given volume that the required degree of close proximity is achieved.

A composite material comprising cells immobilised in a permeable gel supported on a support material (e.g. a cloth or mesh) may be prepared as disclosed in British Patent Application No. 8126579 and used to produce chemical compounds in accordance with the present invention.

Thus, a composite material comprising a support material carrying a permeable gel containing viable cells maintained in close proximity may be contacted with a suitable feed solution in a batch-wise manner (e.g. in a shake-flask) or may be contacted with a suitable feed solution in a continuous flow-through system. In the latter case, the composite material can be contained in a column vessel thereby to produce a "reactor" through which a suitable feed solution may be passed.

In either the batch-wise or flow through manner of contacting, chemical compounds excreted by the cells can be subsequently recovered from solution.

In accordance with a further preferred embodiment of the present invention there is provided a process for the production of a chemical compound by use of cells comprising contacting a feed solution with a composite material comprising a support material, a permeable gel retained on the support material and, immobilised in the permeable gel, viable cells, said cells being maintained in sufficiently close proximity by the permeable gel to cause the cells to excrete a chemical compound produced in the cells, and recovering the chemical compound substantially without damage to the said cells.

The permeable gel may be, for example, a modified poly acrylamide gel prepared as disclosed in Examples 17 and 18 of co-pending Application No. 8126579 hereinbefore mentioned.

A feed solution in accordance with the present invention may optionally contain nutrient material for the cells (e.g. growth hormone deficient nutrient material such as Gamborg B5 medium) and, if desired, precursors (e.g. tryptophan) for the chemical compound it is desired to produce.

It will be appreciated that any solution or liquid contacted with the cells should be such that substantially no damage is done to the cells.

A wide range of chemical compounds can be produced in accordance with the present invention by the appropriate choice of cells.

Thus, the following are examples of chemical compounds which may be prepared using plant cells: steroid drugs, 'alkaloid' drugs, natural biocides, natural colourings, flavourings and aromas.

Animal cells (e.g. produced by tissue culture) may be used in accordance with the present invention in the production of, for example, proteins.

By way of example, Vinca cells (which are eukaryotic cells) have been immobilised in a modified acrylamide gel produced as disclosed in Examples 17 and 18 of co-pending Application No. 8126579 and have been used in the production of cell free ajmalicine and serpentine.

The composite of Vinca cells immobilised in this modified acrylamide gel has been shown to be stable to calcium complexing agents.

Examples of plant cells which may be used in the production of a chemical compound in accordance with the present invention are:

*Catharanthus roseus* (Vinca), Cinchona and Papaver which respectively can produce the alkaloid drugs serpentine, quinine and codeine; Diascorea and Digitalis which respectively produce the steroid drugs diosgenin and digoxin; cells producing the natural biocides phytoallexins and Ribes which produce the natural colouring ribene. It will be appreciated that quinine produced by Cinchona can also be used as a flavouring.

Examples of animal cells which may be used in the production of a chemical compound in accordance with the present invention are myelomas which produce antibodies.

Hybrid cells may be used to produce antibodies.

A convenient upper limit for cell density in accordance with the present invention has been found to be ~35 g/65 g of gel (i.e. ~0.53/1g of gel). Above this cell density the strength of the gel can become deleteriously affected.

When using cells immobilised in a permeable gel in accordance with the present invention the lower limit of cell density is governed by the capacity for chemical compound production. A convenient lower limit for cell density has been found to be ~5 gwt/35 g gel (i.e. ~0.14 g/1g of gel).

It is believed, but not certain, that the excretion of chemical compound by cells is "triggered" by cell derived "messenger compounds". Thus, when cells are held in sufficiently close proximity the concentration of "messenger compounds" becomes such that the behaviour of the cells is affected in such a way that chemical compounds are excreted by the cells.

Thus, it is believed that maintenance in close proximity in accordance with the present invention may "mimic" conditions which may exist in a whole plant or animal body. Further it appears that the build up of the required concentration gradients is not possible in cultures (e.g. a suspension culture) and also it is not possible continuously to draw off chemical compound product by frequent changes of media to encourage further secretion.

It will be noted that higher cell densities (i.e. closer proximity) appear to be necessary for the excretion of chemical compounds when cells are contained in a bag then when cells are immobilised in a gel.

A possible explanation for this is that when cells are immobilised in a gel the diffusion of "messenger compounds" is restricted. Thus messenger compounds do not quickly diffuse from the environment of the cells with the result that the "triggering" concentration of messenger compounds "required to promote chemical compound excretion may be reached at a lower cell density than is required when using "free" cells where the "messenger compounds" are more readily lost (i.e. when using free cells a higher cell density is required to achieve the "triggering concentration").

In accordance with the present invention it has been found that Vinca cells held in a woven nylon bag at an effective density of 0.5 g/ml of continent volume produce extra cellular alkaloid when incubated in 100 ml of Gamborg B5 medium lacking hormone.

The production of extracellular alkaloid was observed with effective cell densities down to 30 g per 100 ml of containment volume.

In accordance with the present invention it has also been found that Vinca cells immobilised in a permeable gel (as hereinbefore mentioned) produce extracellular alkaloid at a cell density of 5 g weight wt/35 g of gel. Vinca cells have also been observed to produce extracellular alkaloid in accordance with the present invention at cell density of 35 g wet wt/65 g of gel.

In comparative experiments it was found that Vinca cells growing freely in Gamborg B5 medium containing benzyladenine, indolyl acetic acid as a hormone and 5% surcrose achieved wet weight densities of at least 20 g/100 ml medium without excreting alkaloid.

Vinca cells grown freely in Gamborg B5 medium containing 24D as hormone were not observed to produce extracellular alkaloid. Furthermore Vinca cells grown in Gamborg B5 medium lacking hormone were not observed to produce extracellular alkaloid at cell densities up to 20 g/100 ml.

According to another aspect of the present invention there is provided a composite material, suitable for use in the production of a chemical compound, comprising a support material and, immobilised on the support material, viable cells, said cells being at a point in their growth cycle where secondary metabolism is established such that the chemical compound can be produced in the cells and said cells being maintained in sufficiently close proximity that the cells can excrete the chemical compound produced in the cells.

In accordance with one embodiment of the immediately preceding aspect of the invention there is provided a composite material, suitable for use in the production of a chemical compound, comprising a support material, a permeable gel retained on the support material and, immobilised in the permeable gel, viable cells, said cells being at a point in their growth cycle where secondary metabolism is established such that the chemical compound can be produced in the cells and said cells being maintained in sufficiently close proximity by the permeable gel that the cells can excrete the chemical compound produced in the cells.

It is to be understood that the composite material can be "active" (i.e. can be such that the production and excretion of chemical compounds is in progress) or, optionally the composite material can be such that the production and excretion of chemical compounds is substantially suspended (e.g. by freezing) for example for storage and/or transport. The composite material can be subsequently "activated" by being subjected to conditions (such as those hereinbefore disclosed) which enable the cells to produce and excrete chemical compounds.

According to a further aspect of the present invention there is provided a method for the preparation of a composite material, suitable for use in the production of a chemical compound, which comprises growing cells to a point in their growth cycle where secondary metabolism is established such that the chemical compound can be produced in the cells and immobilising the cells as viable cells on a support material, the concentration of the cells being selected such that the cells are maintained in sufficiently close proximity by the permeable gel that the cells can excrete the chemical compound produced in the cells.

In accordance with one embodiment of the immediately preceding aspect of the present invention there is provided a method for the preparation of a composite material, suitable for use in the production of a chemical compound, which comprises growing cells to a point in their growth cycle where secondary metabolism is established such that the chemical compound can be produced in the cells and forming on a support material a permeable gel containing the cells, thereby to immobilise the cells as viable cells, the concentration of the cells being selected such that the cells are maintained in sufficiently close proximity by the permeable gel that the cells can excrete the chemical compound produced in the cells.

It is to be understood that the composite material optionally can be treated after formation such that the production and excretion of chemical compounds is substantially suspended (e.g. by freezing) for example for storage and/or transport. The composite material can be subsequently "activated" by being subjected to conditions (such as those hereinbefore disclosed) which enable the cells to produce and excrete chemical compounds.

It is preferred that the cells are immobilised by a method disclosed in co-pending British Patent Applications Nos. 8126579 or 8126580 as hereinbefore mentioned.

The present invention is of wide applicability and finds application in a wide range of biological syntheses and transformations.

As hereinbefore disclosed, cells which do not excrete chemical compounds in free suspension can be induced to excrete chemical compounds by being maintained in sufficiently close proximity in accordance with the present invention. It is believed that the present invention can also find application with cells which are capable of excreting chemical compounds in free suspension; thus, it is believed that the ability of such cells to excrete chemical compounds may be enhanced by maintaining such cells in close proximity in accordance with the present invention.

The present invention may be used in the production of cell-free chemical compound products. In accordance with the present invention it is possible to exercise control of the micro-environment of the cells.

According to yet a further aspect of the present invention there is provided apparatus, suitable for use in the production of a chemical compound, including a container and, located in the container, viable cells containing the chemical compound said cells being maintained in sufficiently close proximity to cause the cells to excrete the chemical compound.

The present invention also provides a chemical compound whenever prepared by a process in accordance with the present invention.

Also the invention provides a composite material suitable for use in the production of a chemical compound whenever prepared in accordance with the present invention.

The present invention will now be further described, by way of example only, by reference to the following Examples. (All solutions and reagents contacted with the cells in these Examples were sterile and all operations involving the cells were performed aseptically).

EXAMPLE 1

A sterile solution of 0.75% xanthan gum, in 0.1M phosphate buffer (pH 6.0; 20 g) was mixed with 30% w/v acrylamide/0.75% methylene bis acrylamide in the same buffer (10 ml) and nitrogen gas bubbled through for 3 minutes. Vinca cells grown in suspension culture for 14 days using Gamborg B5 medium containing benzyladenine and indolyl acetic acid as hormone and 5% sucrose, were filtered on nylon mesh.

9 g of these wet cells were suspended in the xanthan acrylamide mixture and 10% ammonium persulphate (0.6 ml) and 10% TEMED (0.6 ml) was added.

The resulting mixture was immediately transferred to a sterile nylon bag containing a sheet of J-cloth (14½×18cm) and clamped in a frame with the bag confined in a space ⅛" wide. After 15 minutes the resulting gel sheet composite was removed and washed in Gamborg B5 medium (2×250 ml) for a total period of 35 minutes.

EXAMPLE 2

The gel sheet composite prepared in Example 1 was cut into convenient strips and placed in a flask containing 100 ml of sterile B5 medium lacking hormones. After incubation for 2 days on an orital shaker at 25° the strips were transferred to a fresh B5 medium (no hormones). This procedure was repeated over a period of 130 days with flask changes at 2-4 day intervals. The alkaloid content of the supernatants was determined by High Pressure Liquid Chromatography using a Microbondapak column. The cumulative amounts of extracellular ajmalicine and serpentine are shown in FIG. 1.

EXAMPLE 3

A sterile solution of 15% w/v acrylamide, 0.38% w/v methylene bisacrylamide in 0.1M phosphate buffer pH6 (10 ml) was mixed with a sterile aliquot of 2½% w/v sodium alginate solution in water (Sigma 20 g) and the mixture was purged with sterile nitrogen for 3 minutes. Vinca cells grown in suspension culture for 14 days, using Gamborg B5 medium containing benzyladenine and indolyl acetic acid as hormones and 5% w/v sucrose, were vacuum filtered on nylon mesh.

15 g of these cells were added to the acrylamide/alginate mixture, followed by 10% v/v TEMED solution (0.5 ml) and 10% w/v ammonium persulphate solution (0.5 ml). The resulting mixture was stirred and immediately transferred to a sterile, nitrogen purged nylon bag containing a sheet of J-cloth (18×14 ½cm) and clamped in a frame with the bag confined to a space ⅛" wide. After 15 minutes the resulting gel sheet composite was removed and washed in 300 ml Gamborg B5 medium (lacking hormone but containing an additional 0.09% calcium chloride) for 20 minutes. The cloth was then transferred to 300 ml of fresh Gamborg B5 medium (lacking hormone but containing an additional 0.09% calcium chloride) for a further 1 hour to complete gel formation and washing.

EXAMPLE 4

The gel sheet composite prepared as in Example 3 was cut into convenient strips and placed in a flask containing 100 ml Gamborg B5 medium lacking hormones. After incubation for 2 days on an orbital shaker at 25° C. the strips were transferred to fresh B5 medium-lacking hormones. This procedure was repeated over a period of 16 days with flask changes at 2-4 day intervals. The alkaloid content of the supernatants was determined by High Pressure Liquid Chromatography using a Microbondapak column.

The mean daily rate of appearance of serpentine in the medium over this period was 16 μg and 16 μg for a replicate.

The mean daily rate of appearance of ajmalicine in the medium over this period was 26 μg and 29 μg for a replicate.

EXAMPLE 5

Vinca cells which had been grown in suspension culture for 17 days using Gamborg B5 medium containing benzyladenine and indolyl acetic acid as hormones and 5% w/v sucrose, were vacuum filtered on nylon mesh. 15 g of these cells were placed in sterile rectangular bag 10×3.5cm, made of 200 mesh woven nylon material. The bag had an effective volume of 30 ml. The mouth of the bag was folded over and sealed with a Mediclip (Medicell International Ltd.).

EXAMPLE 6

The sealed bag prepared as in Example 5 was placed in a flask containing 100 ml Gamborg B5 medium lacking hormones. After incubation for 2 days on an orbital shaker at 25° C. the bag was transferred to fresh B5 medium lacking hormones. This procedure was repeated over a period of 16 days with flask changes at 2-4 day intervals. The alkaloid content of the used medium was determined by High Pressure Liquid Chromatography using a Microbondapak column.

The mean daily rate of appearance of serpentine in the medium over this period was 23 μg and 21 μg for a replicate.

The mean daily rate of appearance of ajmalicine in the medium over this period was 30 μg and 26 μg for a replicate.

We claim:

1. A process for the production of a chemical compound by use of plant cells comprising maintaining viable plant cells, containing intra-cellular secondary metabolites, in sufficiently close proximity by immobilizng the cells in a modified polyacrylamide gel comprising polyacrylamide having added to it a minor amount of a polymeric material selected from the group consisting of xanthan gum and sodium alginate, to cause the cells to excrete the intra-cellular secondary metabolites and recovering the secondary metabolites substantially without damage to the cells.

2. A process as claimed in claim 1 wherein the cells to be maintained in sufficiently close proximity to cause the cells to excrete the secondary metabolites are cells which are at a point in their growth cycle wherein secondary metabolism is established.

3. A process as claimed in claim 1 wherein the cells to be maintained in sufficiently close proximity to cause the cells to excrete the secondary metabolites are cells which are before a point in their growth cycle where any substantial senescence occurs.

4. A process as claimed in claim 1 wherein cells to be maintained in sufficiently close proximity to cause the cells to excrete the secondary metabolites are cells which have reached a point in their growth cycle corresponding to the logarithmic to mid-logarithmic phase.

5. A process as claimed in claim 1 wherein the cells to be maintained in sufficiently close proximity to cause the cells to excrete the secondary metabolites are cells which have been contacted with a feed solution under conditions that produce the secondary metabolites.

6. A process as claimed in claim 1 wherein the cells are immobilised in said modified polyacrylamide gel by a method which comprises applying a modified polyacrylamide gel precursor containing minor amounts of xanthan gum or sodium alginate to a support material, the said gel precursor containing said cells, and gelling the modified polyacrylamide gel precursor to form a composite material comprising the support material, said modified polyacrylamide gel retained on the support material and said cells immobilised in the gel, the rheological properties of the gel precursor being selected (i) to facilitate application of the gel precursor to the support material and (ii) to facilitate retention of the gel precursor on the support material prior to and during the gelling and/or to inhibit the sedimentation of cells prior to, and during gelling.

7. A process as claimed in claim 1 wherein the plant cells are selected from the group consisting of Catharanthus roseus (Vinca) cells, Cinchona cells, Papaver cells, Diascorea cells, Digitalis cells, cells capable of producing the natural biocides phytoallexins, and Ribes cells.

8. A process as claimed in claim 1 wherein the secondary metabolite produced is a steroid drug, an alkaloid drug, a natural biocide, a natural colouring, a flavouring, an aroma or a protein.

9. A composite material suitable for use in the production of intra-cellular secondary metabolites, comprising a support material, a permeable modified polyacrylamide gel retained on the support material and, viable plant cells immobilised in the permeable gel, said modified polyacrylamide gel containing a minor amount of a polymeric material selected from the group consisting of xanthan gum and sodium alginate, said cells being at a point in their growth cycle where secondary metabolism is established such that the intra-cellular secondary metabolites can be produced in the cells and said cells being maintained in sufficiently close proximity by the permeable gel that the cells can excrete the intra-cellular secondary metabolites produced in the cells.

* * * * *